United States Patent [19]

Hellstrom

[11] Patent Number: 5,343,296
[45] Date of Patent: Aug. 30, 1994

[54] OPTICAL SCANNER WITH SELF CONTAINED STANDARDIZATION MEANS

[75] Inventor: Ake A. Hellstrom, Columbus, Ohio

[73] Assignee: ABB Process Automation Inc., Columbus, Ohio

[21] Appl. No.: 13,565

[22] Filed: Feb. 4, 1993

[51] Int. Cl.⁵ .................... G01N 21/17; G01N 21/86
[52] U.S. Cl. .................... 356/431; 356/436
[58] Field of Search ............. 356/429, 430, 431, 446, 356/432; 250/252.1, 341

[56] References Cited

U.S. PATENT DOCUMENTS

| | | | |
|---|---|---|---|
| 4,288,160 | 9/1981 | Lodzinski | 356/429 |
| 4,319,847 | 3/1982 | Howarth | 356/431 |
| 4,748,400 | 5/1988 | Typpo | 324/61 |
| 4,766,315 | 8/1988 | Hellstrom et al. | 250/339 |
| 4,767,935 | 8/1988 | Anderson et al. | 250/571 |
| 4,786,817 | 11/1988 | Boissevain et al. | 250/571 |
| 4,801,809 | 1/1989 | Burk et al. | 250/559 |
| 4,879,471 | 11/1989 | Dahlquist | 250/359.1 |
| 4,950,911 | 8/1990 | Williams et al. | 250/563 |
| 5,019,710 | 5/1991 | Wennerberg et al. | 250/341 |
| 5,073,712 | 12/1991 | Hellstrom | 250/252.1 |

*Primary Examiner*—Rolf Hille
*Assistant Examiner*—David B. Hardy
*Attorney, Agent, or Firm*—Chilton, Alix & Van Kirk

[57] ABSTRACT

An apparatus for optically scanning and measuring the physical parameters of a sheet material by means which are fully enclosed within an air purged cross-machine box-beam structure to protect the radiation source, the radiation detector and the optics from the harsh machine environment. The apparatus may involve a single beam enclosing a combined source/detector module for reflection measurement or dual beams on opposite sides of the sheet for transmission measurement with one enclosing a source module and the other enclosing a detector module. Standardization means are also provided either in the module itself or as an extension of the beam. Means are also disclosed for sealing the opening in the beams through which the radiation passes.

20 Claims, 6 Drawing Sheets

OPTICAL SCANNER WITH SELF CONTAINED STANDARDIZATION MEANS

BACKGROUND OF THE INVENTION

The present invention relates to an advanced infrared scanner and more particularly to a scanner having traversing scanner heads completely located inside of a box-beam structure.

There are many situations where it is desirable to have a scanner for a moving web, such as in a paper machine, where space limitations and the environment prohibit the use of currently available scanner structures. For example, there are no scanners which are compact enough to fit into the wet press section of a modern paper machine. During the 1960's and 1970's, the emerging scanning technology was attempted in the press sections of board and linerboard paper machines. The reliability due to the environment was poor, the measurements were slow and inaccurate and the installation was difficult. As the machine speeds increased during the 1980's, and as new pressing schemes for substantially higher levels of water removal were realized, the machine space for conventional wet press scanners was not available. In addition, the environment became even more hostile with higher temperatures and water sprays making the application of available scanning sensors with exposed sensor heads impractical.

SUMMARY OF THE INVENTION

This invention provides apparatus for measuring physical parameters of sheet material by directing electromagnetic radiation from a source to the sheet material and detecting the responses associated with the interaction of the radiation with the sheet material.

An object is to provide a scanning optical (visible or infrared) sensing device which is fully enclosed within a cross-machine beam structure forming a scanner apparatus which has a small cross-sectional area and where the sensor module is protected from the machine environment. More particularly, an object of the present invention is to provide a self-supporting box-beam in which the sensor module is fully contained and protected. An object is also to provide a scanning optical sensing device which may be of the reflection measurement type with a box-beam on only one side of the sheet material containing both the radiation source and the radiation detector or of the transmission measurement type with box-beams on each side of the sheet material with one containing the source and the other containing the detector.

A further object is to provide a scanning sensor module with self contained standardization means and means for air purging the beam and sensor module to prevent the entry of environment contaminants.

DESCRIPTION OF THE PREFERRED EMBODIMENTS

Figure 1:
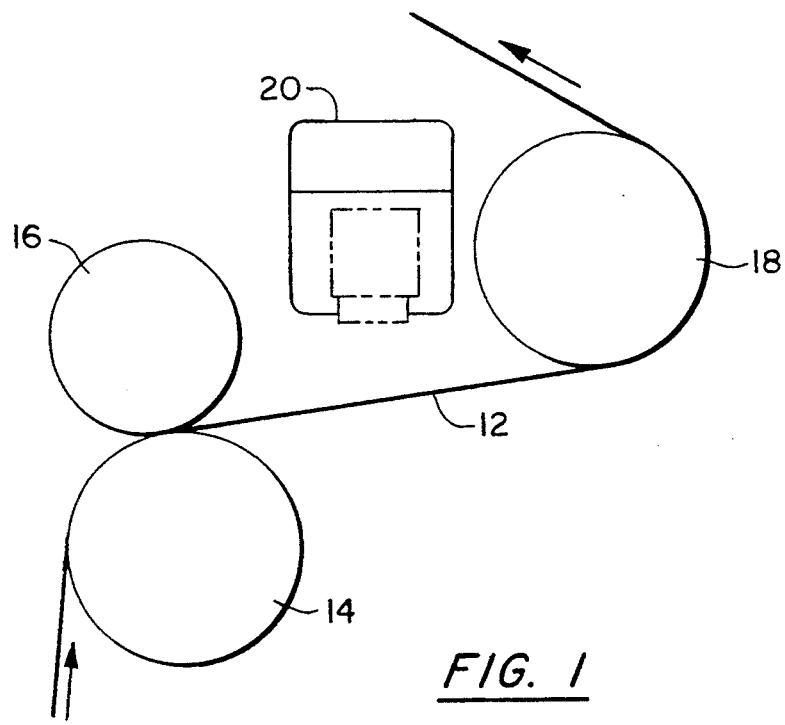
FIG. 1 is a simplified view of a portion of a web forming or treating apparatus incorporating a scanning apparatus of the reflection measurement type according to the present invention.

FIG. 1 is a general, simplified view of a section of an apparatus in which a web of material 12 is being fed through the feeding and or supporting rollers 14, 16 and 18 in the direction indicated by the arrows. Extending across the machine adjacent to the web is the scanning apparatus 20. Most typically, the invention would be applied to a paper making machine but the invention is applicable to the scanning and measurement of any web of material that one would desire to optically scan.

Figure 2:
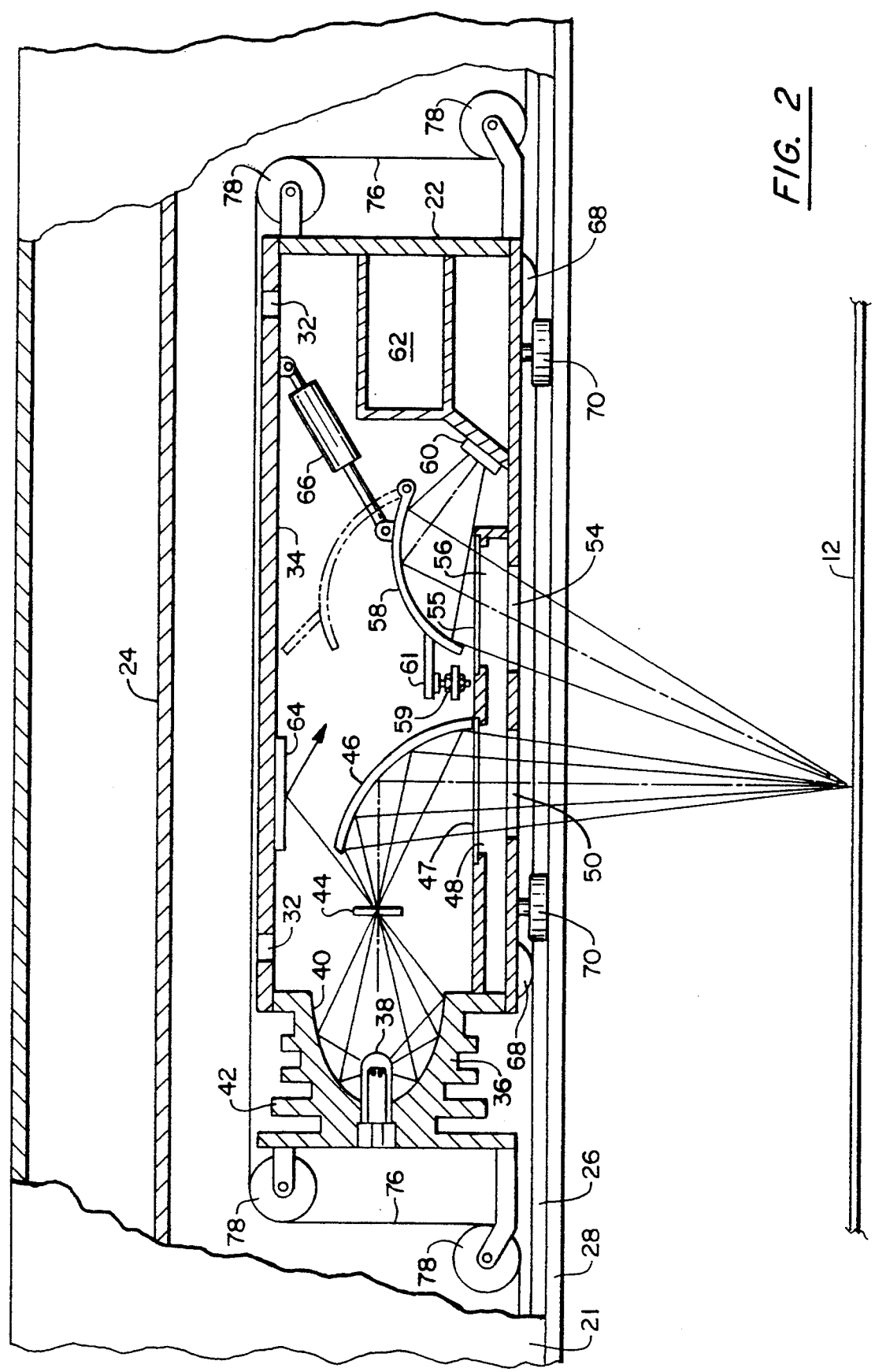
FIG. 2 is a cut-a-way side view of a scanner beam housing the scanner of the present invention with the scanner being shown in cross section.
Figure 3:
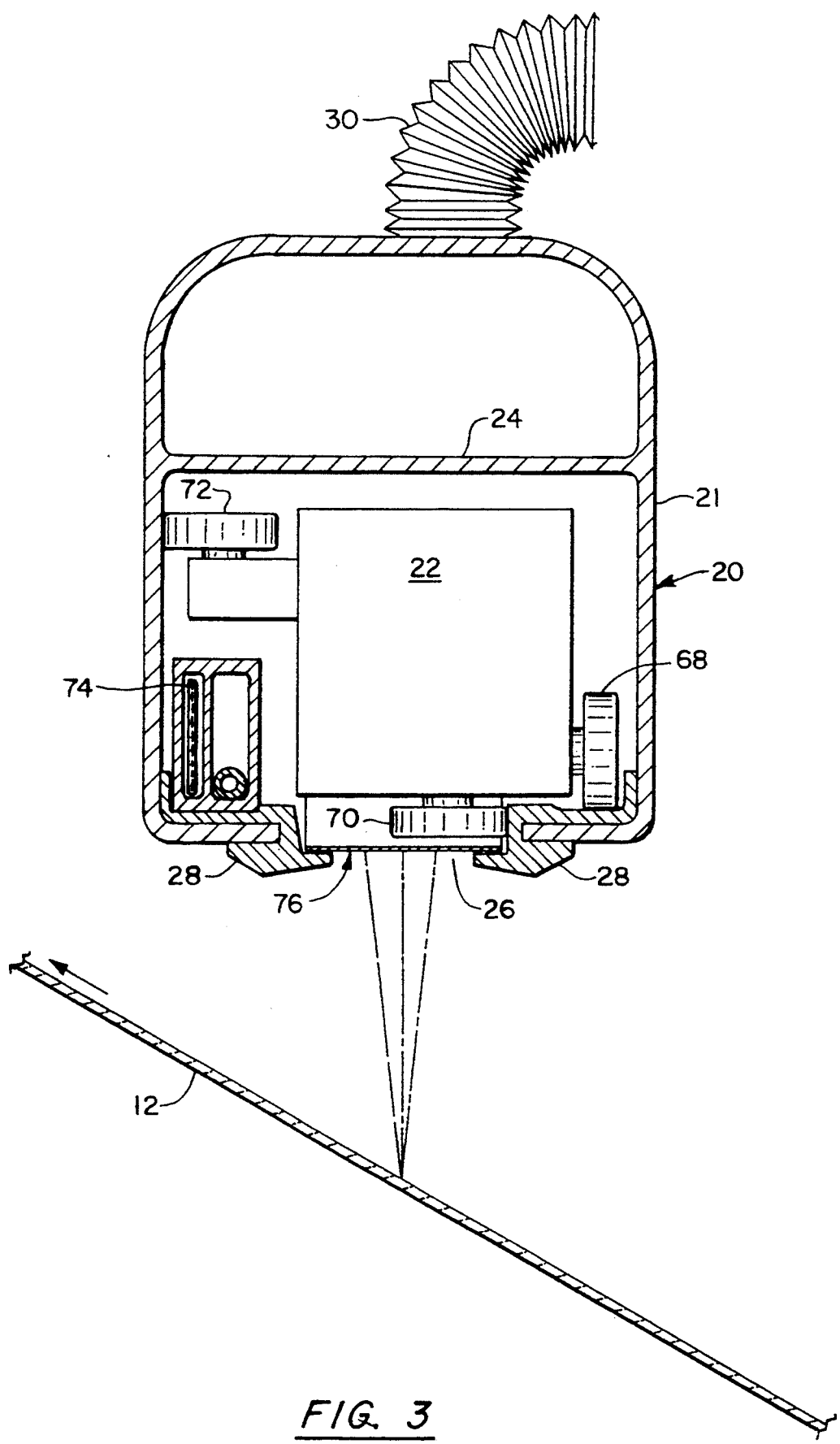
FIG. 3 is a cross section of a scanner beam illustrating the end view of the scanner housed within the beam.

Referring now to FIG. 2, the scanning apparatus 20 comprises a beam 21. A portion of the beam 21 is shown with a section being cut-a-way to show the interior of the beam and the scanner module 22. The cross section of the beam is shown in FIG. 3. The beam 21, referred to as a box-beam, of the machine and the web to be measured, is supported only at the ends and is sufficiently rigid so that it will not sag. To provide this rigidity, the beam is formed generally in the shape of a box as seen in FIG. 3 with a supporting cross-member or web 24. As an example, the beam would be constructed of 10 mm steel plate and welded or extruded of an aluminum alloy to the desired cross-section for vertical, horizontal and torsional strength. The beam 21 would be appropriately supported at the ends by structures not shown. The beam has an opening 26 in the bottom thereof running substantially the full length of the beam or, more accurately, the full length of the scan to be performed. Attached along each edge of the opening 26 are the carriage tracks 28. These tracks fit over the edges of the opening 26 and define the optical scanning aperture as well as provide the guiding surfaces for smooth traversing of the sensor module carriage and flexible cables.

In order to prevent the entry of contaminants into the beam and into the sensor module, an air purge system is provided. Purging air is introduced into the beam 21 through the duct 30 as shown in FIG. 3. The cross-member or web 24 does not extend all the way to the end of the beam so as to provide air flow throughout the entire beam. Some of the air flows around the module 22 and out the opening 26 while the remaining air flows into the module through holes 32 and then out of the module and out the opening 26. This air purge provides a positive pressure in the beam and module and thus air flow out through the opening 26 to prevent the flow of contaminants in through opening 26. In addition, the air purge provide cooling of the module.

Turning now to the module construction, it comprises a housing 34 with a source lamp module 36 mounted at one end. The source lamp module 36 comprises a source lamp 38, an elliptical reflector 40 and cooling fins 42. The source lamp 38 provides the source of electromagnetic radiation over a spectral band that includes the infrared region. Mounted within the housing 34 and located at the focal point of the elliptical reflector is a chopper 44 which may be a motor driven rotating disk, an electronically-driven tuning fork or any other device suitable for modulating the radiation beam. A tuning fork is preferred for its stability, low cost and low heat generation.

The modulated radiation is primarily directed to the elliptical mirror 46 from which it is reflected through the glass 47 covering the opening 48, through the opening 50 in the bottom of the housing 34, through the opening 26 and down onto the web 12. The web 12 is the web of paper or other material being scanned. This optical system utilizing the mirror enables the radiation beam to be focused onto the sheet while allowing a suitable standoff distance between the sensor module and the web. This distance (from the web 12 to the beam 20) might be on the order of 0.1 to 0.5 meters (4 to 20 inches) thus fully eliminating the possibility of contact with the web.

The radiation beam is reflected off of the web as shown in FIG. 2 and reflects up through the openings 26 and 54, the glass 55 in opening 56 and onto the elliptical mirror 58. From the elliptical mirror 58, the radiation is reflected onto the detector 60. The angle of the radiation from the mirror 46 to the web is such that the radiation does not impinge on the web at a 90° angle thus avoiding specular reflection. Likewise the angle between the web and the radiation reflected from the web to mirror 58 is not 90° for the same reasons. In the other direction as shown in FIG. 3, the beam 21 is tilted with respect to the plane of the web which is again to avoid specular reflection. The detector 60 is preferably a standard multi-channel sensor which then feeds the measurement reading to the conventional electronics in the compartment 62. For more details on a multi-channel detector, see U.S. Pat. No. 4,766,315. The final measurement signals are then fed out from the scanner beam in a conventional manner. In order to provide for variations in the distance from the sensor module to the web being measured, means are included for changing the angular position of mirror 58. This comprises an adjustable hard-stop 59 and extension 61 on the mirror. In it normal measuring position. The extension 61 engages the hard-stop so that the angle of mirror 58 is proper to project the radiation onto the detector 60. To focus the sensor for a desired web to sensor distance, the hard stop 59 is adjusted to change the mirror angle and maintain the proper focus angle.

For standardization purposes, a standardization sample 64 is attached inside of the housing 34 in a position such that a portion of the radiation from the lamp 38 and reflector 40 are directed past the mirror 46 and onto the sample 64. This radiation is scattered from the sample 64 and onto the detector 60 when the mirror 58 is pivoted up out of its normal position into the standardization position shown in dotted lines in FIG. 2. For this purpose, a positioning device 66 such as a solenoid is attached to the housing 34 and the mirror 58. This positioning device would be programmed to activate at any desired time interval or position across the scan.

The sensor module 22 is mounted within the beam 21 on the wheels 68, 70 and 72 as best seen in FIG. 3. These wheels are positioned such that they will maintain the module in its precise orientation and permit the module to be easily rolled while scanning. A known and conventional flexible cable scan operating mechanism 74 is enclosed within the beam 21 and attached to the sensor module 22 to move the sensor module back and forth through its scanning pattern.

In addition to the internal pressurization of the beam and as a means for enhancing the effectiveness of the pressurization, a sealing tape or belt 76 is incorporated to cover the opening 26. This sealing belt is attached at each end of the beam 21 and merely lays in the tracks 28 as shown in FIG. 3. As shown in FIG. 2, this sealing belt extends up and over the sensor module 22 and is engaged by the rollers 78. Therefore, as the sensor module 22 scans back and forth, it picks up the sealing belt from the tracks and then places it back down into the tracks. Because the sealing belt seals the opening 26 except in the immediate vicinity of the scanner module at any particular time and location in its scan, less purge air flow is required and the velocity of the purge air out from the beam is increased.

Although the optics have been shown and described as including the elliptical mirrors 46 and 58 and the glass 48 and 56, other arrangements could be used for focusing the measurement energy onto the web. For example, flat mirrors could be used instead of the elliptical mirrors and the glass covers 47 and 55 replaced with appropriate lenses.

Figure 4:
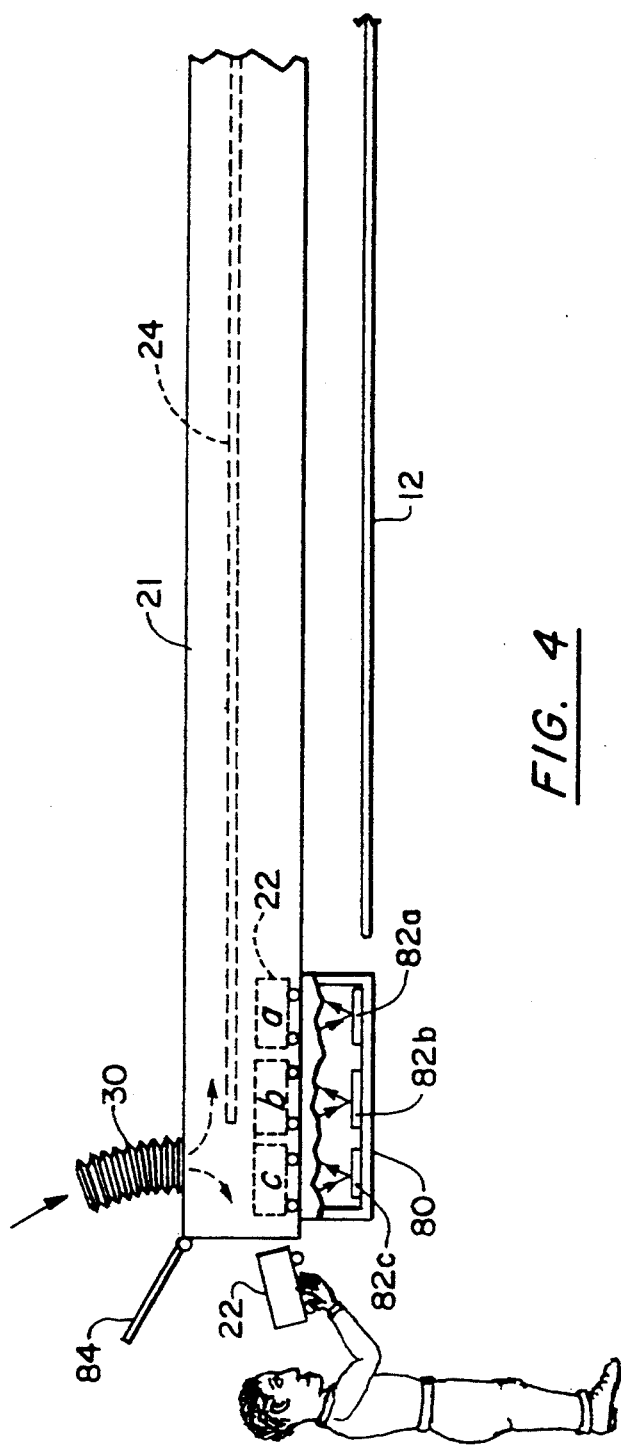
FIG. 4 is a simplified front view of a scanner beam illustrating an alternate standardization arrangement and the serviceability of the unit.
Figure 8:
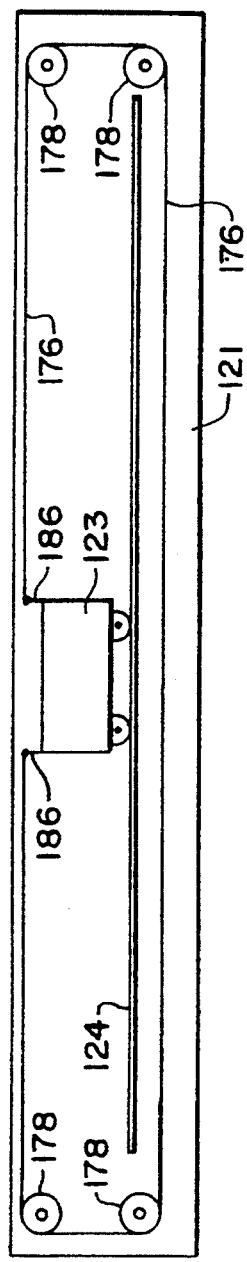
FIG. 8 is a simplified front view of the detector beam of FIG. 6 illustrating the sealing belt arrangement.
Figure 6:
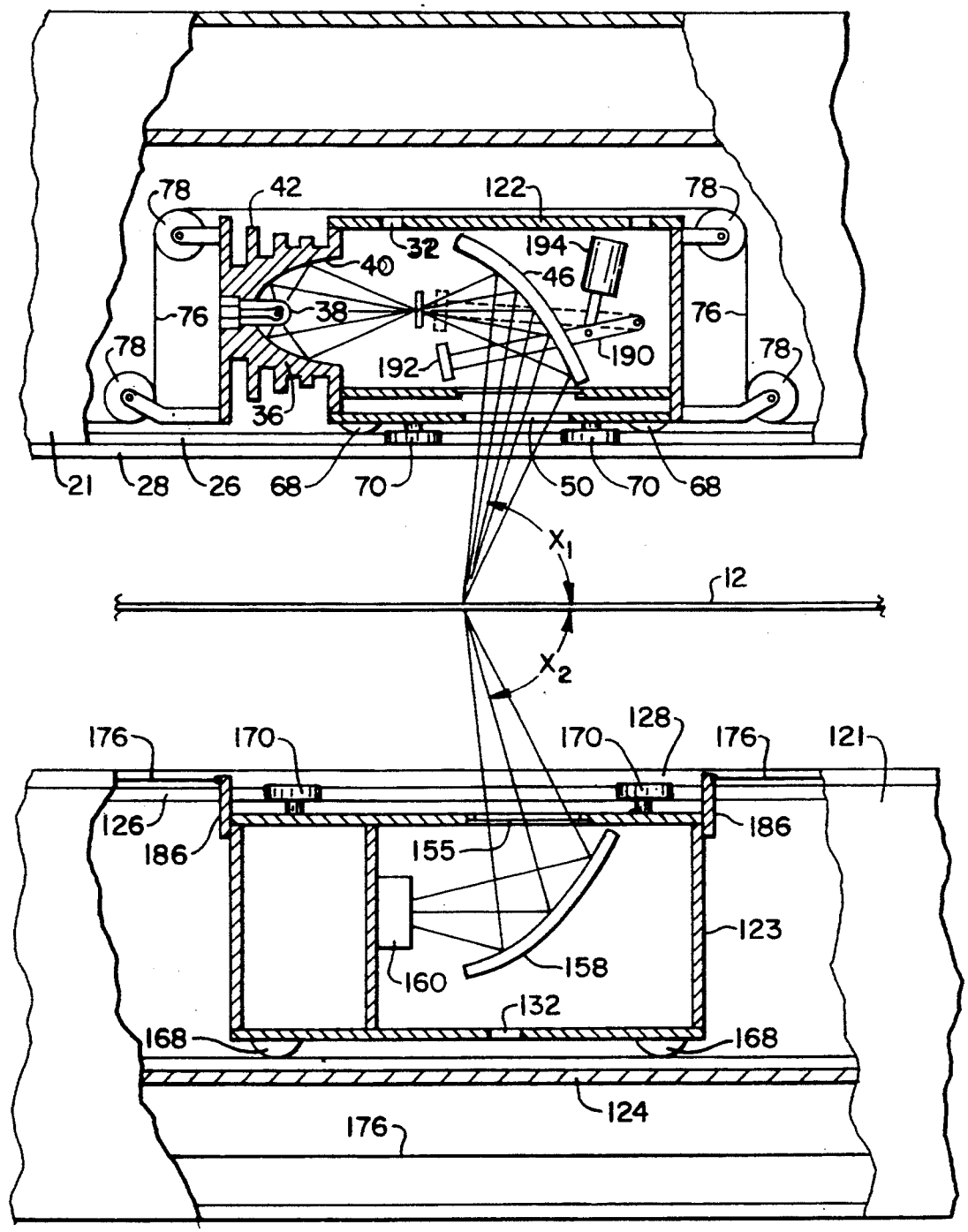
FIG. 6 is a cut-away side view of a scanner apparatus of the transmission type.
Figure 7:
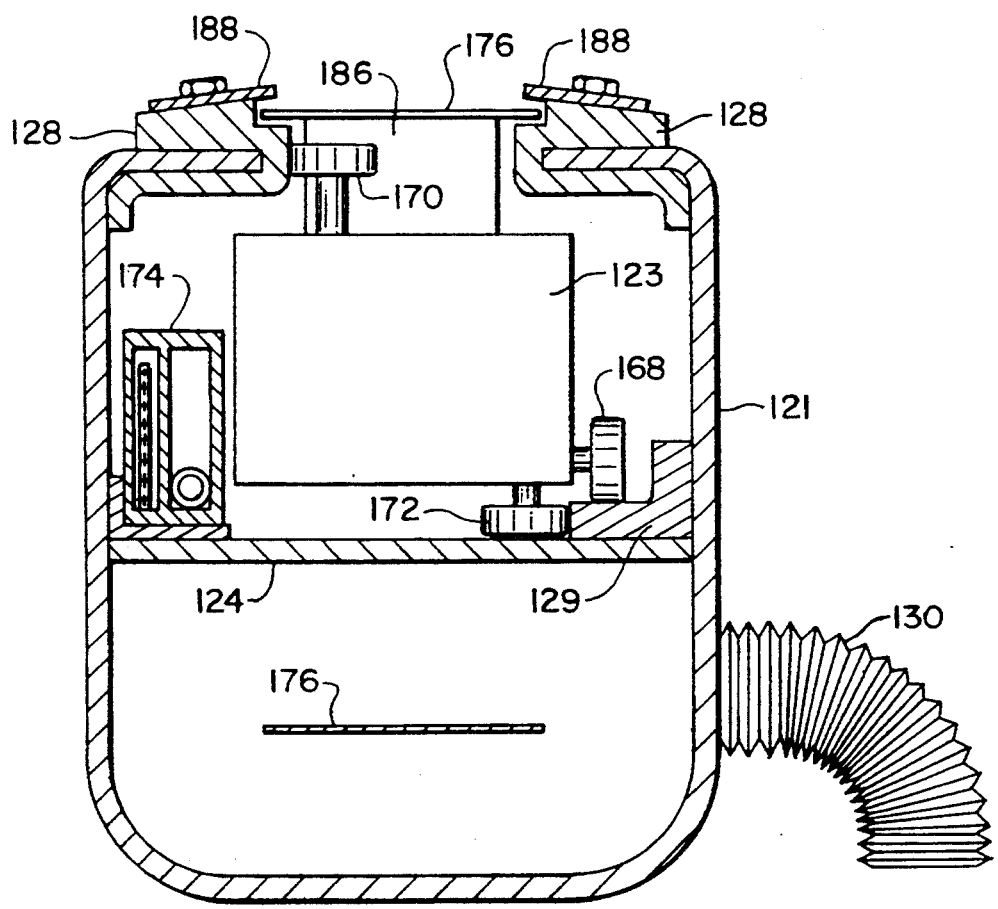
FIG. 7 is a cross-section view of the detector beam and module of FIG. 6.

FIG. 4 illustrates an alternate or supplemental arrangement for standardization. At the end of the beam 21 which extends out beyond the edge of the web 12, there is an enclosed standardization sample box 80. This box is open to the beam 21 and to the opening 26 (see FIGS. 2 and 3) and the box contains one or more standardization samples 82. These samples are true calibration samples which, for example, may be paper encapsulated in glass. As shown, the sensor module 22 will pass over and scan the three illustrated samples a, b and c when it is in the respective positions a, b and c. In this arrangement, the samples are protected from the environment just as the interior of the beam is protected. The system will periodically restrict the sensor to the positions a, b and c to read the samples for purposes of standardization. Such an arrangement would have been difficult to implement with conventional scanners with sensor heads external to the beam because of the inability to completely protect the sample from dust, water and temperature of the environment.

FIG. 4 also illustrates another feature of the invention which is the ready access to the sensor module for service. Since the environment in which the device is typically installed is hostile and unfriendly to personnel as well as being cramped, safe access for service is important. Since the sensor module is a self-contained unit entirely within the beam and riding on a track system, it can readily be detached from the flexible drive and the customary electrical connections and then merely removed as a unit out from the end of the beam. FIG. 4 shows an open access door 84 and the module being removed. Since this end of the beam is extended out from the web processing area, the access area is likewise somewhat remote from the hostile environment.

Figure 5:
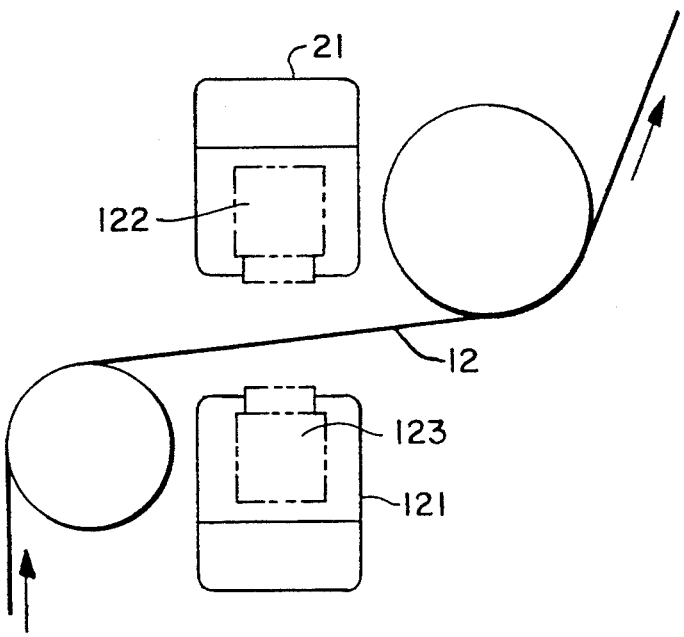
FIG. 5 is a view similar to FIG. 1 incorporating a scanning apparatus of the transmission measurement type.

Referring now to FIGS. 5 to 8, an alternate form of the present invention relates to a transmission (through the web) mode of operation rather than a reflection mode. Numbered parts in the 100 series are similar to the part numbers in the previous embodiment. As shown in FIG. 5, the beam 21, which now contains only the source module 122, is located on one side of the web 12 and the detector module 123 in beam 121 is located on the other side of the web. The beam contains a cross-member 124. The source module 122 no longer contains the detector and its associated components and contains a different standardization arrangement which will be explained hereinafter.

The radiation reflected from the mirror 46 is focused on the web 12 and is transmitted through the web. The transmitted radiation as effected by the properties of the web to be measured enters the slit opening 126, goes through the glass 155 and is intercepted by the elliptical mirror 158 and focused onto the detector 160. To detect only the scattered light, the angles $x_1$ and $x_2$ are both less than 90° so that is no direct, straight line light path from the source to the detector. The detector module is movably supported by the wheels 168, 170 and 172 on the tracks 128 and 129. The detector module is driven by the flexible cable operating mechanism 174 which is coordinated in a known manner with the drive for the source module 122. The beam 121 would also be air purged at 130 in the same manner as beam 20. Likewise, the detector module has air purge holes 132 to admit the purge air into the detector module.

Because of gravity, the bottom beam 121 has a different arrangement for the sealing belt 176. The sealing belt 176 forms a loop with the two ends being fastened to the detector module 123 such as by the extensions 186. The sealing belt is captured into a recess in the tracks 128 and retained in position by the plates 188. The operation of the sealing belt 176 can be seen in the schematic FIG. 8. As the detector module moves back and forth, the sealing belt 176 moves with it since it is attached to the detector module at 186. The sealing belt merely forms a loop around the rollers 178.

As previously indicated, the standardization arrangement for this transmission embodiment differs from the standardization for the reflection mode of operation. Mounted in the source module on the pivot arm 190 is a standard transmission sample 192. By means of the pneumatic or other cylinder 194, the sample is pivoted up into the path of the radiation as shown by the dotted lines in FIG. 6. This is done at a point in the seam when the scanner is off-web. In this position, the radiation transmitted to the detector is the radiation transmitted through the sample thereby facilitating calibration. It is also noted that the alternate or supplemental standardization or calibration scheme as shown in FIG. 4 for the reflection method scanner is also applicable to a transmission scanner. In this case, the externally sealed sample housing 80 will extend between the two beams and include a transparent bottom in such a way that energy from the source to the detector has to pass through the samples 82 a, b, c when the sensors are at the corresponding positions. As can be seen from the description of the invention, it provides a system for optically measuring the properties of a web or sheet material by means of a small, compact scanning system with either one beam containing both the source and the detector or with two beams with one containing the source and the other containing the detector with the modules being totally located inside of box-beams. Since the modules are compact, the beams may be small, taking into consideration the structural requirements of supporting the beam across the web, and can be installed in locations where other, larger, prior scanner apparatus would not fit. As an example of size reduction, a typically prior art scanner might occupy a cross-sectional box area of 0.30 $m^2$ whereas the present invention (reflection type) would typically occupy 0.07 $m^2$. Furthermore, the design permits the location of the scanner in harsh environments since it is totally enclosed inside the beam and is air purged. There are no external exposed sensor parts or moving members. The use of the mirrors of the invention to focus the radiation onto the web allows a suitable standoff distance from the beam to the web with no contact. Standardization is simplified by means either fully contained within the sensor module or contained in an extension of the beam which is fully protected from the environment.

What is claimed is:

1. In a system for measuring optical properties of a moving web of sheet material by projecting electromagnetic radiation onto the moving web and detecting the electromagnetic radiation after interaction with the moving web comprising:

a first beam mounted to extend parallel to one face of the moving web in a cross-machine direction, said beam being generally hollow and including an elongated opening through the side of said first beam adjacent the moving web;

an electromagnetic radiation source module mounted entirely inside of said first beam adjacent said elongated opening; and means for traversing said source module back and forth within said first beam along said elongated opening, and wherein said source module comprises:

a. a housing having an aperture adjacent said elongated opening for passing electromagnetic radiation through said aperture and said elongated opening;

b. a source of electromagnetic radiation within said housing; and c. optical means within said housing including an elliptical mirror to receive and focus said radiation from said source through said aperture and through said elongated opening onto the moving web.

2. In a system as recited in claim 1 wherein said housing includes a second aperture and wherein said source module further includes detector means and second optical means to receive radiation reflected from the moving web and passed through said elongated opening and said second aperture and to focus said reflected radiation onto said detector means.

3. In a system as recited in claim 2 wherein said second optical means comprises a second elliptical mirror.

4. In a system as recited in claim 3 and further including a standardization sample mounted in said housing whereby a portion of said radiation is scattered off of said sample as a standard radiation onto said detector means and wherein said second mirror is movable between a first position to focus radiation from said moving web onto said detector and block said standard radiation from said detector and a second position in which radiation from said moving web is not focused onto said detector and said standard radiation is reflected onto said detector.

5. In a system as recited in claim 3 and further including means for adjusting said second mirror to adjust the focus of reflected radiation from said web onto said detector for varying web positions.

6. In a system as recited in claim 4 and further including means for adjusting said second mirror to adjust the focus of reflected radiation from said web onto said detector for varying web positions.

7. In a system as recited in claim 1 and further including means for purging said first beam and said source module with air comprising means for introducing air into said first beam and for introducing air from said first beam into said source module under pressure whereby air flows out from said source module through said aperture and out from said first beam through said elongated opening.

8. In a system as recited in claim 2 and further including standardization means off-web adjacent one end of said first beam, said standardization means comprising an enclosed housing attached to said first beam over said elongated opening and containing at least one standardization sample whereby radiation from said source module focuses onto said standardization sample when said source module is in a standardization position and reflects a standard radiation to said detector.

9. In a system as recited in claim 7 and further including sealing means covering said elongated opening in said first beam and including means for moving said sealing means to permit said source module to traverse back and forth between said sealing means and said elongated opening.

10. In a system as recited in claim 1 and further including access means at one end of said beam to permit removal of said source module.

11. In a system as recited in claim 1 and further including a second beam mounted to extend parallel to the other face of the moving web in said cross-machine direction in line with said first beam, said second beam being generally hollow and including an elongated opening through the side of said second beam adjacent the moving web; an electromagnetic radiation detector module mounted entirely inside of said second beam including means to traverse said detector module back and forth within said second beam along said elongated opening; and means for traversing said detector module and wherein said detector module comprises:
   a. a detector housing having an aperture adjacent said elongated opening for passing electromagnetic radiation in through said elongated opening and said aperture;
   b. a detector for detecting said electromagnetic radiation mounted in said detector housing; and
   c. optical means mounted in said detector housing to receive said radiation transmitted through said moving web from said source module and focus said radiation onto said detector.

12. In a system as recited in claim 11 wherein said optical means mounted in said detector housing comprises a mirror.

13. In a system as recited in claim 12 wherein said mirror is an elliptical mirror.

14. In a system as recited in claim 11 and further including a standardization transmission sample, said standardization transmission sample mounted so as to be movable into the paths of said radiation whereby a standard radiation is transmitted to said sample.

15. In a system as recited in claim 14 wherein said standardization sample is located in said source module.

16. In a system as recited in claim 15 wherein said standardization sample is mounted on a pivotal arm to pivot said standardization sample into the path of said radiation.

17. In a system as recited in claim 11 and further including standardization means off-web adjacent one end of said first and second beam, said standardization means comprising an enclosed housing attached to one of said first and second beams over said elongated opening to pass radiation therethrough and containing at least one standardization sample whereby said source module focuses radiation onto and through said standardization sample to said detector module when said source and detector modules are in a standardization position.

18. In a system as recited in claim 11 wherein said second beam and said detector module comprises means for introducing air into said second beam and for introducing air from said second beam into said detector module under pressure whereby air flows out from said detector module through said aperture in said detector module and out from said second beam through said elongated opening.

19. In a system as recited in claim 11 and further including sealing means covering said elongated opening in said second beam, said sealing means attached to said detector module and movable therewith.

20. A system for measuring optical properties of a moving web of sheet material comprising:
   a beam mounted to extend parallel to one face of the moving web in a cross-machine direction, said beam having a generally rectangular cross section, being generally hollow and including an elongated opening through the side of said beam adjacent the moving web, and
   a sensor module mounted entirely inside of said hollow beam, said sensor module and means for traversing said source module back and forth within said beam along said elongated opening, said sensor module comprising:
   a. a housing having first and second apertures adjacent said elongated opening for passing electromagnetic radiation through said apertures and said elongated opening;
   b. a source of electromagnetic radiation within said housing;
   c. a fixed elliptical mirror within said housing to receive and reflect a first portion of said radiation from said source through said first aperture and through said elongated opening and to focus said radiation onto the moving web;
   d. a second elliptical mirror within said housing pivotally mounted to move between a first and second position to receive said radiation reflected from said web through said elongated opening and said second aperture;
   e. detector means within said housing to receive radiation from said second elliptical mirror in said first position and convert said received radiation to a signal indicative of said optical property; and
   f. a standardization sample mounted within said housing to receive a second portion of said radiation from said source and reflect said radiation onto said detector when said second elliptical mirror is pivoted to said second position, and means for pivoting said second elliptical mirror between said first and second positions.

* * * * *